United States Patent [19]

Kijima et al.

[11] 4,175,139

[45] Nov. 20, 1979

[54] HYPERTENSION TREATING AGENT CONTAINING POLYPRENYL ALCOHOL

[75] Inventors: Shizumasa Kijima, Tokyo; Isao Yamatsu, Kawaguchi; Yuichi Inai, Tokyo; Toshiji Igarashi, Tokorozawa; Yoshikage Nakajima, Tokyo, all of Japan;

[73] Assignee: Eisai Co., Ltd., Tokyo, Japan

[21] Appl. No.: 931,687

[22] Filed: Aug. 7, 1978

[30] Foreign Application Priority Data

Aug. 10, 1977 [JP]  Japan .................................. 52-94965
Nov. 8, 1977 [JP]  Japan .................................. 52-133008

[51] Int. Cl.² ............................................ A61K 31/45
[52] U.S. Cl. .................................................. 424/343
[58] Field of Search ................ 424/343; 568/844, 845

[56] References Cited

U.S. PATENT DOCUMENTS

| | | | |
|---|---|---|---|
| 3,440,292 | 4/1969 | Allen ..................................... | 568/845 |
| 3,911,025 | 10/1975 | Henrick et al. ........................ | 568/844 |
| 4,059,641 | 11/1977 | Mishima et al. ...................... | 424/343 |
| 4,116,955 | 9/1978 | Ichikawa et al. ................ | 260/455 R |

*Primary Examiner*—Douglas W. Robinson
*Attorney, Agent, or Firm*—Blanchard, Flynn, Thiel, Boutell & Tanis

[57] ABSTRACT

This invention relates to a hypertension treating agent comprising a polyprenyl alcohol or an ester thereof of the general formula:

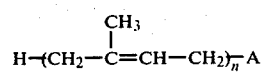

wherein n represents an integer of 7–10 and A represents a group of the general formula:

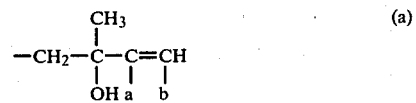

(a)

in which a and b each represent hydrogen or they may form a bond, or

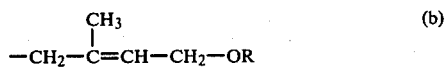

(b)

in which R represents hydrogen or —COR', R' being a saturated or unsaturated aliphatic hydrocarbon group of 1–17 carbon atoms; cyclohexyl group; unsubstituted phenyl group or phenyl group substituted with a halogen atom or a lower alkoxy group; (halogen atom-substituted phenoxy)-lower alkyl group; or pyridyl group.

15 Claims, 4 Drawing Figures

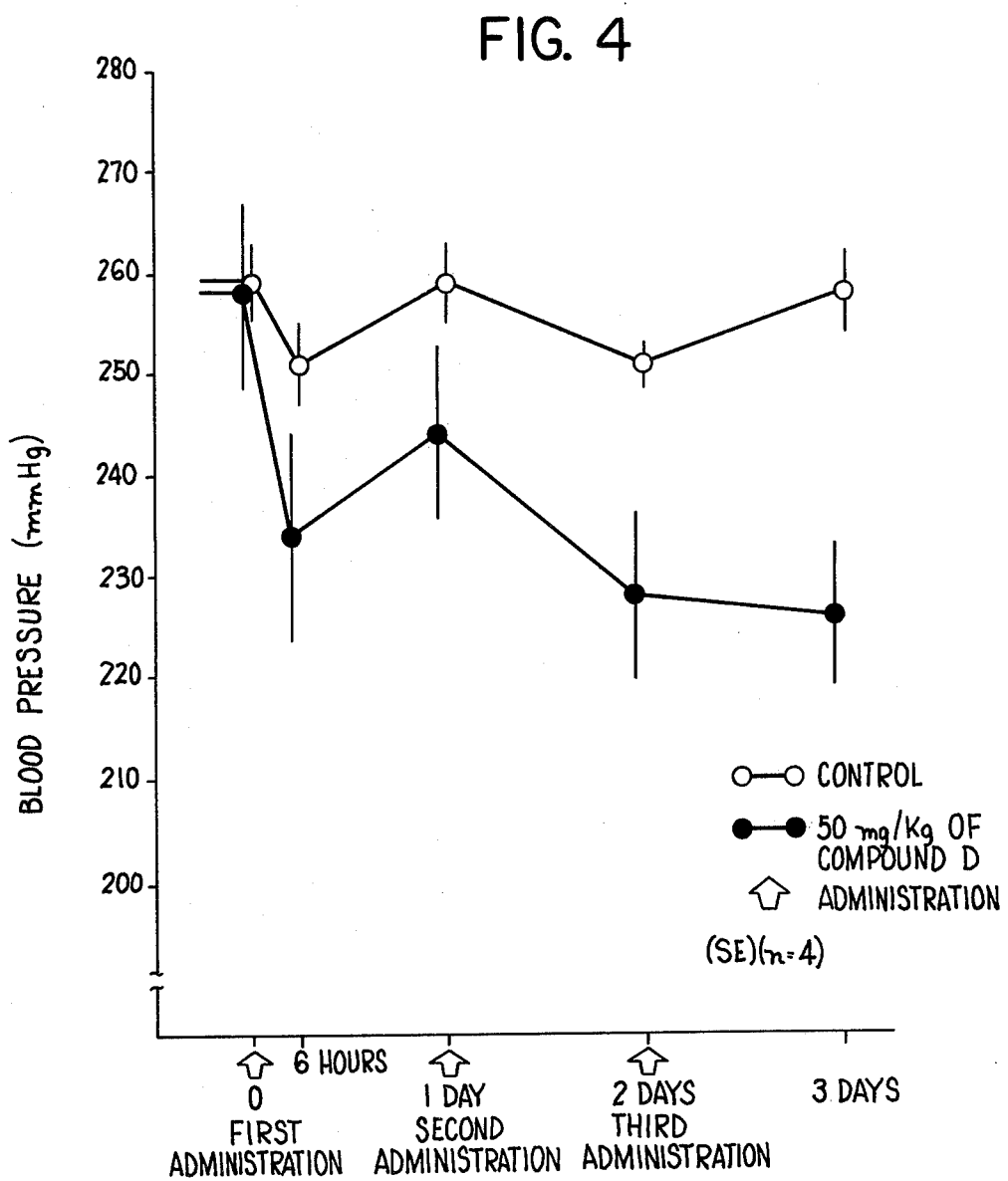

HYPERTENSION TREATING AGENT CONTAINING POLYPRENYL ALCOHOL

BACKGROUND OF THE INVENTION

1. FIELD OF THE INVENTION

This invention relates to a hypertension treating agent comprising a polyprenyl alcohol or its ester.

2. DESCRIPTION OF PRIOR ARTS

Various hypertension treating agents have been used for treating hypertension. However, those agents are accompanied with various harmful side effects and, therefore, there are problems in the administration of those agents particularly when they are administered in a large amount continuously over a long period of time. For example, diuretic hypotensors such as sulfonamide preparations and thiazide preparations have serious side effects of causing hyperuricacidemia and hypokalemia: sympatholytic agents such as reserpine preparations and methyldopa preparations have side effects of causing thirst in the mouth, clouding of consciousness and orthostatic hypotension; and vasodilators such as apresoline have side effects of causing headache, tachycardia and angina pectoris. After investigations for the purpose of finding hypotensors of an improved safety, the inventors have found the compounds of the present invention.

SUMMARY OF THE INVENTION

This invention relates to a hypertension treating agent comprising a polyprenyl alcohol or an ester thereof of the general formula:

$$H\text{-}(CH_2\text{-}\underset{\underset{CH_3}{|}}{C}=CH\text{-}CH_2)_n\text{-}A$$

wherein n represents an integer of 7-10, and A represents a group of the general formula:

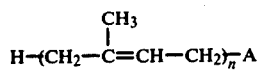  (a)

in which a and b each represent hydrogen or they may form a bond, or

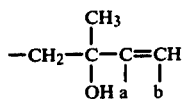  (b)

in which R represents hydrogen or —COR', R' being a saturated or unsaturated aliphatic hydrocarbon group of 1–17 carbon atoms; cyclohexyl group; unsubstituted phenyl group or phenyl group substituted with a halogen atom or a lower alkoxy group; (halogen atom-substituted phenoxy)-lower alkyl group; or pyridyl group.

As the saturated or unsaturated aliphatic hydrocarbon groups of 1–17 carbon atoms in general formula (I), there may be mentioned, for example, methyl, ethyl, propyl, pentyl, hexyl, heptyl, octyl, nonyl, decanyl, undecanyl, dodecanyl, tridecanyl, tetradecanyl, pentadecanyl and hexadecanyl groups as well as related unsaturated groups such as vinyl, propenyl, butenyl, 9-decenyl, 8, 11-heptadecadienyl and 8, 11,14-heptadecatrienyl groups. As the lower alkoxy groups, there may be mentioned, for example, methoxy, ethoxy, propoxy and butoxy groups. As the lower alkyl groups, there may be mentioned, for example, methyl, ethyl, propyl and isopropyl groups. As the pyridyl groups, there may be mentioned 2-, 3- and 4-pyridyl groups.

BRIEF DESCRIPTION OF DRAWINGS

FIG. 4 shows the hypotensive effect of 3,7,11,15,19,23,27,31,35,39-decamethyl-2,6,10,14,18,22,26,30,34,38-tetracontadecaene-1-ol (compound D) of the present invention administered to SHR.

Pharmacological effects and toxicity (acute toxicity) of compounds (I) of the present invention observed in animal tests were as shown below:

PHARMACOLOGICAL TESTS

○ Hypotensive effects on Okamoto & Aoki spontaneous hypertension rats (hereinafter referred to as SHR):

[Method]

Hypotensive effects of test compounds on Okamoto & Aoki SHR were measured. SHR's of chronic hypertension which were 40 weeks old were used as test animals. The maximum blood pressure was about 265 mm Hg. The blood pressure was measured by a Shimazu type continuous blood pressure measuring apparatus (Model SCS-301 manufactured by Shimazu Seisakusho K.K., Japan). The systolic blood pressure was measured on the tail artery without drawing blood.

Test compounds were suspended in acacia. The test animals were divided into groups according to the amount administered of the test compound (50 mg/Kg). Further, a control group in which only aqueous acacia solution was given was tested similarly. Each group consisted of 4 test animals. The test compounds were orally administered to SHR once a day for three days continuously.

The blood pressure was measured before the administration and thereafter at points of 6 hours, 24 hours (at the time of the second administration), 48 hours (at the time of the third administration) and 72 hours and the change of the blood pressure with the passing of time was examined.

[Test Compounds]

3,7,11,15,19,23,27,31,35,39-Decamethyl-1,6,10,14,18,22,26,30,34,38-tetracontadecaene-3-ol (hereinafter referred to as compound A):

3,7,11,15,19,23,27,31-octamethyl-2,6,10,14,18,22,26,30-dotriacontaoctaene-1-ol (hereinafter referred to as compound B);

3,7,11,15,19,23,27,31,35-nonamethyl-2,6,10,14,18,22,26,30,34-hexatriacontanonaene-1-ol (hereinafter referred to as compound C); and 3,7,11,15,19,23,27,31,35,39-decamethyl-2,6,10,14,18,22,26,30,34,38-tetracontadecaene-1-ol (hereinafter referred to as compound D).

[Results]

Figure 1:
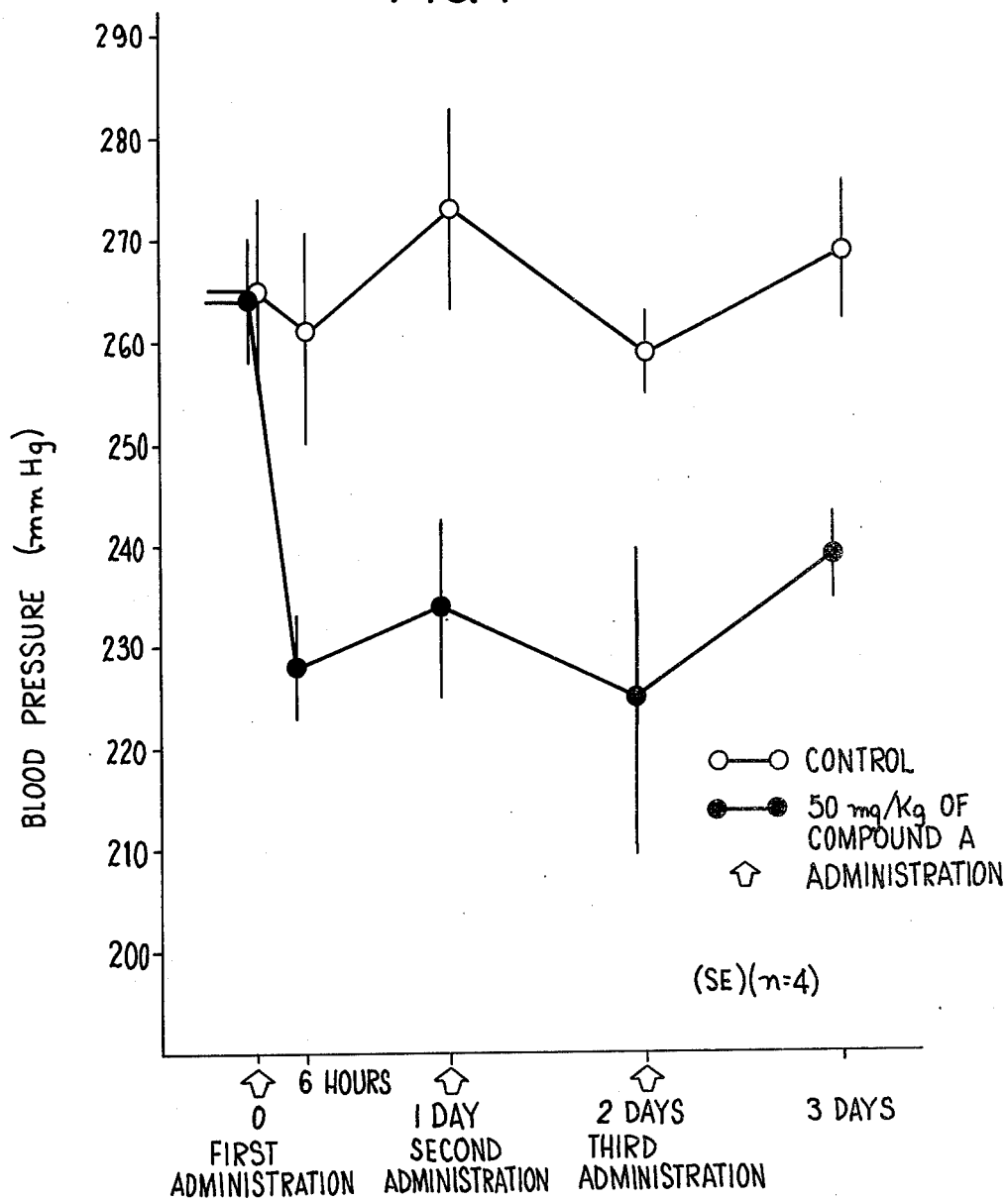
FIG. 1 shows the hypotensive effect of 3,7,11,15,19,23,27,31,35,39-decamethyl-1,6,10,14,18,22,26,30,34,38-tetracontadecaene-3-ol (hereinafter referred to as compound A) of the present invention administered to spontaneous hypertension rats.
Figure 2:
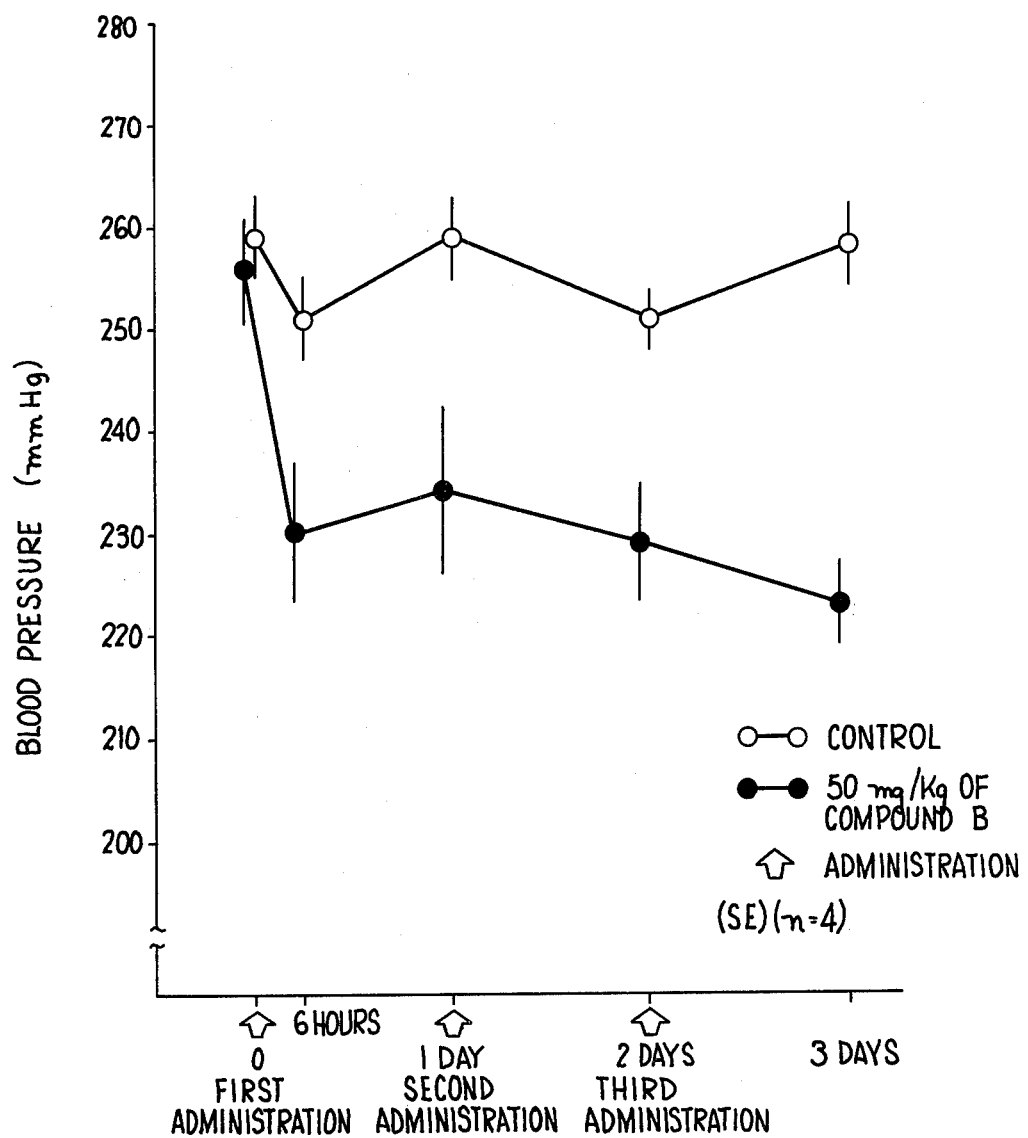
FIG. 2 shows the hypotensive effect of 3,7,11,15,19,23,27,31-octamethyl-2,6,10,14,18,22,26,30-dotriacontaoctaene-1-ol (compound B) of the present invention administered to spontaneous hypertension rats (hereinafter referred to as SHR).
Figure 3:
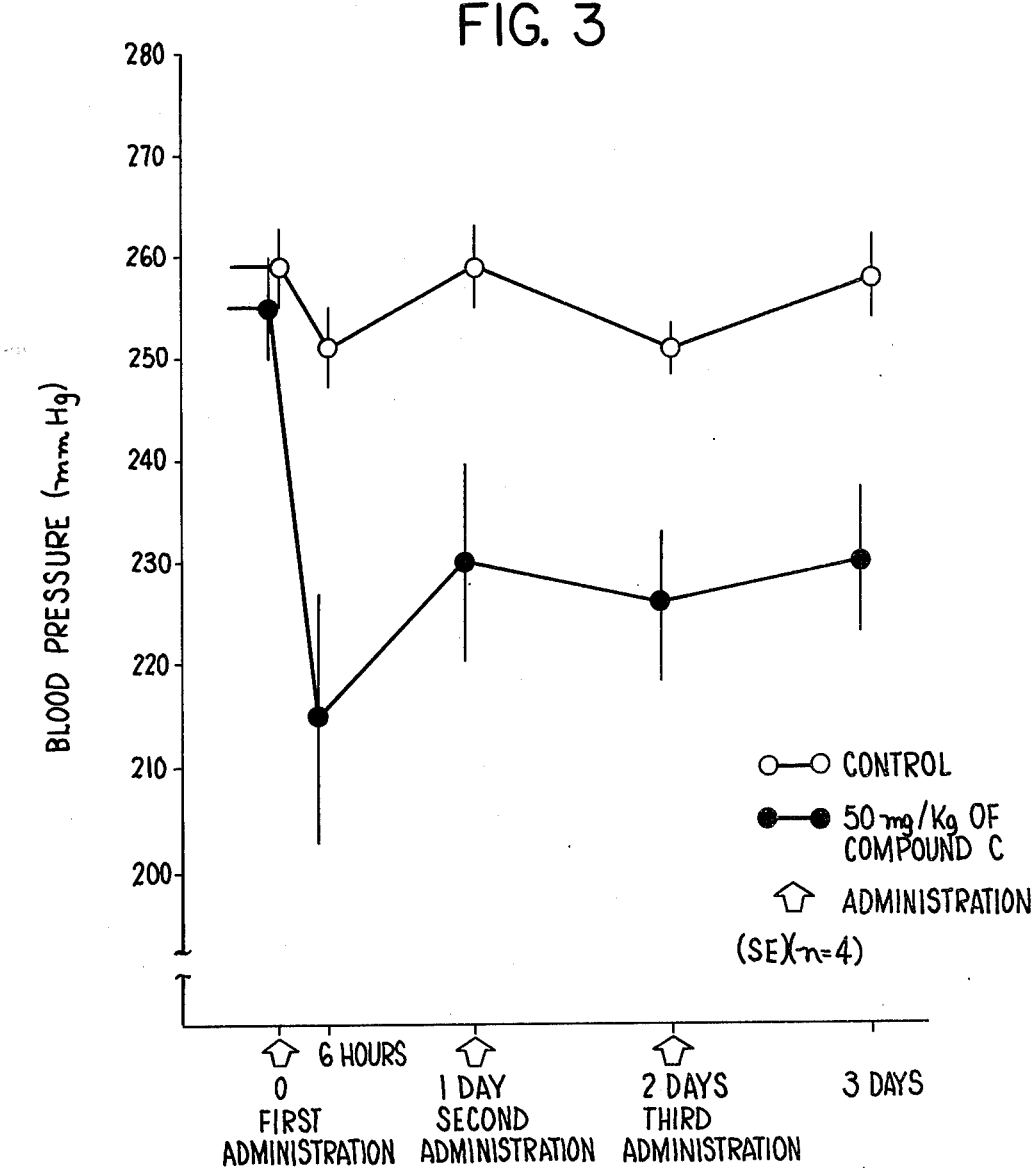
FIG. 3 shows the hypotensive effect of 3,7,11,15,19,23,27,31,35-nonamethyl-2,6,10,14,18,22,26,30,34-hexatriacontanonaene-1-ol (compound C) of the present invention administered to SHR.

Clear hypotensive effects as shown in FIGS. 1-4 were recognized in the groups of the test animals (Okamoto & Aoki SHR's) to which 50 mg/Kg of compound A, B, C or D was administered orally for three days continuously. For example, a clear hypotensive effect was recognized in a group of the test animals to which 50 mg/Kg of compound A was administered orally for three days continuously as shown in FIG. 1. The rats in the control group (initial blood pressure: 265 mg) exhibited substantially no change in blood pressure after three days' experiment period (blood pressure after the experiment: 269 mmHg). In the group to which compound A was administered, blood pressure of 264 mm Hg before the test was reduced to 228 mm Hg 6 hours after the first administration and to 234 mm Hg 24 hours after the first administration (i.e. at the time of the second administration). Thus, a continuous hypotensive effect was recognized.

In the group of rats to which compound B was administered, the blood pressure of 256±5 mm Hg at the initial stage of the test was reduced to 230±7 mm Hg 6 hours after the first administration and 234±8 mm Hg 24 hours after the first administration (i.e. at the time of the second administration), while in the control group, the blood pressure of 259±4 mm Hg at the initial stage of the test was insignificantly changed to 258±4 mm Hg after the three days of the experiment period.

Thus, it is evident that compounds, A, B, C and D have remarkable continuous hypotensive effects.

TOXICITY TESTS

SD Rats (male and female weighing about 200 g) were used as test animals. 500 mg/Kg of the test compounds was administered orally in the same manner as in the pharmacological tests described above. No death or side effect was recognized.

As will be apparent from the above results of pharmacological tests and toxicity tests, compounds of general formula (I) of the present invention are very effective for the prevention and treatment of renal hypertension, endocrine hypertension, cardiovascular hypertension, nervous hypertension, essential hypertension and the like. The amounts of compounds of general formula (I) of the present invention to be administered and the administration methods are appropriately chosen and adjusted depending on the conditions of the diseases to be medically treated. In general, in case of oral administration to adults, they are given in an amount of 10-200 mg, preferably 50-100 mg, per day.

Compounds of general formula (I) of the present invention can be formed in pharmaceutical compositions according to conventional techniques.

Those compositions are prepared by using an optional pharmaceutical carrier or excipient and are administered according to a conventional method.

It is preferred that the pharmaceutical composition be administered in a form suitable for absorption through the stomach and intestinal ducts. As the oral administration form including a unit dose, there may be mentioned tablets and capsules. These tablets and capsules may comprise binders such as a syrup, acacia, gelatin, sorbitol, tragacanth gum and polyvinylpyrrolidone; excipients such as lactose, sugar, corn starch, calcium phosphate, sorbitol and glycine, disintegrators such as potato starch; and pharmaceutically acceptable wetting agents such a sodium lauryl sulfate as used ordinarily. The tablets may be coated according to methods known in the art. Liquid preparations for oral administration may be aqueous and oily suspensions, solutions, syrups, elixiers and the like. Further, they may be dry products which are to be re-dissolved in water or other suitable vehicles before the administration. These liquid preparations may comprise additives ordinarily used in this field, for example, suspending agents such as sorbitol, syrups, methylcellulose, glucose/sugar syrups, gelatin, hydroxyethylcellulose, hydroxypropylcellulose, calcium carboxymethylcellulose, aluminum stearate gels and hydrogenated edible fats; emulsifiers such as lecithin, sorbitan mono-oleate and acacia; non-aqueous vehicles such as almond oil, fractionated coconut oil, oil esters, propylene glycol and ethyl alcohol; and antiseptics such as methyl p-hydroxybenzoate, propyl p-hydroxybenzoate and sorbic acid.

An injection composition is provided in the form of an ampoule containing a unit administration amount or in the state filled in a multiadministration unit amount vessel together with an antiseptic additive. The composition may be a suspension, a solution or an emulsion in an oily or aqueous vehicle, and it may further comprise a surfactant, stabilizer or the like.

Compounds (I) used for attaining the object of the present invention include both known compounds and compounds unknown prior to the filing date of the present patent application (new compounds). As the new compounds, there may be mentioned, for example, the following compounds which are prepared by processes described below:

SYNTHESIS EXAMPLE 1

3,7,11,15,19,23,27,31,35,39,43-Undecamethyl-6,10,14,18,22,26,30,34,38,42-tetratetracontaundecaene-3-ol 0.24 Gram of metallic magnesium ribbon was added to 20 ml of dry tetrahydrofuran. Then, vinyl chloride gas was introduced therein till the metallic magnesium ribbon was dissolved. The solution was added dropwise with a solution of 5 g of decaprenylacetone in 20 ml of dry tetrahydrofuran. After completion of the addition, the mixture was allowed to stand overnight, added dropwise with 5 ml of saturated aqueous ammonium chloride solution and then added with 50 ml of n-hexane and further with 30 ml of water. The organic solvent layer thus separated was taken out, washed with water and concentrated. The concentrate was dissolved in 30 ml of acetone and the solution was cooled to 0° C. Thus precipitated crystalline compound of a melting point of 38°-40.0° C. was taken out as the final product. Yield 5.0 g.

| Elementary analysis as $C_{55}H_{90}O$: | | |
|---|---|---|
| | C | H |
| Theoretical (%): | 86.19 | 11.82 |
| Found (%): | 86.13 | 11.80 |

MAS Spectrum: M+ 766

IR Spectrum: (cm$^{-1}$) 3390 (OH), 2950, 1640, 1450, 1380, 1130, 900

NMR Spectrum: (CDCl$_3$, ppm)

| 1.30 | s | 3H | —CH$_3$ |
|---|---|---|---|
| 1.60 | s | 30H | —CH$_3$ |
| 1.65 | s | 3H | —CH$_3$ |
| 2.00–2.20 | m | 41H | —CH$_2$, OH |
| 5.00–6.00 | m | 13H | =CH, =CH$_2$ |

SYNTHESIS EXAMPLE 2

3,7,11,15,19,23,27,31,35,39,43-Undecamethyl-6,10,14,18,22,26,30,34,38,42-tetratetracontadecaene-1-yn-3-ol 0.23 Gram of metallic sodium was added to 150 ml of liquid ammonia at −50° C. Then dry acetylene gas was introduced therein till the reaction phase was changed in color from purple to white. Thereafter, a solution of 3.4 g of decaprenylacetone in 100 ml of dry ethyl ether was added thereto dropwise. After completion of the addition, the reaction mixture was kept at a temperature of from −10° C. to −15° C. for 15 hours. After completion of the reaction, ammonia was distilled out. The residue was added with 10 ml of saturated aqueous ammonium chloride solution, 200 ml of ethyl ether and 100 ml of water successively. The organic solvent layer thus separated was taken out, washed with water and concentrated. The concentrate was purified by column chromatography with 80 g of silica gel in n-hexane/ethyl ether solvent mixture as elution solvent to obtain the final product as yellowish white solid (m.p. 35.5–36.5° C.). Yield: 2.5 g.

| Elementary analysis as C$_{55}$H$_{88}$O: | C | H |
|---|---|---|
| Theoretical (%): | 86.32 | 11.59 |
| Found (%): | 86.27 | 11.63 |

MAS Spectrum: M$^+$ 764
IR Spectrum: (cm$^{-1}$)
3400 (OH), 2950, 2120, 1640, 1450, 1378, 1128, 1030, 900
NMR Spectrum: (CDCl$_3$, ppm)

| 1.30 | s | 3H | —O—C(CH$_3$)— |
|---|---|---|---|
| 1.60 | s | 30H | —CH$_3$ |
| 1.62 | s | 3H | —CH$_3$ |
| 2.02–2.08 | m | 41H | —CH$_2$—, —OH |
| 2.48 | s | 1H | —C≡CH |
| 5.04–5.17 | m | 10H | =CH— |

SYNTHESIS EXAMPLE 3

3,7,11,15,19,23,27,31-Octamethyl-2,6,10,14,18,22,26,30-dotriacontaoctaenyl acetate 4.0 Grams of octaprenol were dissolved in 20 ml of acetic acid anhydride. The solution was added with 2.0 g of anhydrous sodium acetate at room temperature. Then, the mixture was stirred at 100° C. for one hour to complete the reaction. The reaction product was poured in water to decompose excessive acetic acid anhydride. After extraction with n-hexane, the extract was washed with water and concentrated. The concentrate was purified by chromatography with 55 g of silica gel in n-hexane/benzene solvent mixture as elution solvent to obtain white waxy product. Yield: 3.6 g.

| Elementary analysis as C$_{42}$H$_{68}$O$_2$: | C | H |
|---|---|---|
| Theoretical (%): | 83.38 | 11.33 |
| Found (%): | 83.37 | 11.34 |

MAS Spectrum: M$^+$ 604
IR Spectrum: (cm$^{-1}$)
2940, 1745, 1670, 1450, 1385, 1370, 1235, 1030
NMR Spectrum: (CDCl$_3$, ppm)

| 1.56, 1.67 | s | 27H | —C=C—CH$_3$ |
|---|---|---|---|
| 2.00 | m | 28H | —C=C—CH$_2$— |
| 2.03 | s | 3H | O=C—CH$_3$ |
| 4.55 | d | 2H | —C=C—CH$_2$—O |
| 5.07–5.32 | m | 8H | —C=CH— |

SYNTHESIS EXAMPLE 4

3,7,11,15,19,23,27,31,35-Nonamethyl-2,6,10,14,18,22,26,30,34-Hexacontanonaenyl-2-(p-chlorophenoxy)-t-butylate 6.0 Grams of solanesol were dissolved in 30 ml of pyridine. The solution was added dropwise with 15% solution of 4.4 g of 2-(p-chlorophenoxy)-tert-butyric acid chloride in pyridine over 30 minutes. After completion of the addition, the mixture was stirred at room temperature for two hours to complete the reaction. The reaction product was diluted with n-hexane, washed with water and concentrated. The concentrate was crystallized from acetone at −5° C. to obtain the final product as white solid (m.p. 29.5°–30° C.). Yield: 6.5 g.

| Elementary analysis as C$_{55}$H$_{83}$ClO$_3$: | C | H | Cl |
|---|---|---|---|
| Theoretical (%): | 79.81 | 10.11 | 4.28 |
| Found (%): | 79.83 | 10.12 | 4.25 |

MAS Spectrum: M$^+$ 826, 828
IR Spectrum: (cm$^{-1}$)
2950, 1740, 1495, 1450, 1390, 1245, 1180, 825
NMR Spectrum: (CDCl$_3$, ppm)

| 1.56 | s | 6H | O=C—C(CH$_3$) |
|---|---|---|---|
| 1.60, 1.68 | s | 30H | C=C—CH$_3$ |

SYNTHESIS EXAMPLE 5

3,7,11,15,19,23,27,31,35,39-Decamethyl-2,6,10,14,18,22,26,30,34,38-tetracontadecaenyl-3,4,5-trimethoxy benzoate 8.0 Grams of decaprenol were dissolved in 50 ml of pyridine and the solution was added dropwise with 15% solution of 4.8 g of 3,4,5-trimethoxybenzoyl chloride in pyridine at room temperature over 30 minutes. After completion of the addition, the mixture was stirred at room temperature for two hours to complete the reaction. Then, the reaction product was diluted with n-hexane, washed with water and concentrated. The concentrate was purified by column chromatography with 70 g of silica gel in n-hexane/benzene solvent mixture as elution solvent to obtain the final product as white solid (m.p. 32.3–32.8° C.). Yield: 5.0 g

| Elementary analysis as $C_{60}H_{92}O_5$: | C | H |
|---|---|---|
| Theoretical (%): | 80.66 | 10.38 |
| Found (%): | 80.63 | 10.37 |

MAS Spectrum: M+ 892
IR Spectrum: (cm$^{-1}$)
2930, 1715, 1595, 1505, 1455, 1385, 1225, 1010, 765
NMR Spectrum: (CDCl$_3$, ppm)

| | | | |
|---|---|---|---|
| 1.58, 1.67, 1.76 | s | 30H | $-\overset{|}{C}=\overset{|}{C}-CH_3$ |
| 2.00 | m | 36H | $-\overset{|}{C}=\overset{|}{C}-CH_2-$ |
| 3.84 | s | 9H | $-OCH_3$ |
| 4.78 | d | 2H | $-\overset{|}{C}=\overset{|}{C}-CH_2-O$ |
| 5.06–5.41 | m | 10H | $-\overset{|}{C}=CH$ |
| 7.24 | s | 2H | (phenyl-H) |
| 2.02 | m | 32H | $\underset{/}{\overset{\backslash}{C}}=\overset{|}{C}-CH_2-$ |
| 4.64 | d | 2H | $\underset{/}{\overset{\backslash}{C}}=\overset{|}{C}-CH_2-O-$ |
| 5.08–5.26 | m | 9H | $\underset{/}{\overset{\backslash}{C}}=CH-$ |
| 6.92 | m | 4H | (phenyl-H) |

SYNTHESIS EXAMPLE 6

3,7,11,15,19,23,27,31,35-Nonamethyl-2,6,10,14,18,22,26,30,34-hexacontanonaenylcyclohexyl carboxylate 10 Grams of solanesol were dissolved in 50 ml of pyridine and the solution was added dropwise with of 15% solution of 4.6 g of cyclohexylcarboxylic acid chloride in pyridine over 30 minutes. After completion of the addition, the mixture was stirred at room temperature for two hours to complete the reaction. Then, the reaction product was diluted with n-hexane, washed with water and concentrated. The concentrate was purified by chromatography with 80 g of silica gel in n-hexane/benzene solvent mixture as elution solvent to obtain the final product as white solid (m.p. 34.0–35.0° C.). Yield: 6.2 g.

| Elementary analysis as $C_{52}H_{84}O_2$: | C | H |
|---|---|---|
| Theoretical (%): | 84.26 | 11.42 |
| Found (%): | 84.28 | 11.43 |

MAS Spectrum M+ 740
IR Spectrum: (cm$^{-1}$)
2930, 1735, 1670, 1455, 1385, 1175, 1135
NMR Spectrum: (CDCl$_3$, ppm)

| | | | |
|---|---|---|---|
| 1.30 | m | 10H | (cyclohexyl H-H) |
| 1.60, 1.70 | s | 30H | $-\overset{|}{C}=\overset{|}{C}-CH_3$ |
| 1.85–2.05 | m | 1H | (cyclohexyl H, C=O, H) |
| 2.02–2.06 | m | 32H | $-\overset{|}{C}=\overset{|}{C}-CH_2-$ |
| 4.54 | d | 2H | $-\overset{|}{C}=\overset{|}{C}-CH_2-O-$ |
| 5.08–5.30 | m | 9H | $-\overset{|}{C}=CH$ |

SYNTHESIS EXAMPLE 7

3,7,11,15,19,23,27,31,35-Nonamethyl-2,6,10,14,18,22,26,30,34-hexatriacontanonaenyl pentanoate 10 Grams of solanesol were dissolved in 50 ml of pyridine and the solution was added dropwise with 6.5 g of valeric acid anhydride at room temperature over 30 minutes. After completion of the addition, the mixture was stirred at room temperature for 5 hours to complete the reaction. The reaction product was poured in water to hydrolyze excessive valeric acid anhydride. After extraction with n-hexane, the extract was washed with water and concentrated. The concentrate was purified by chromatography with 100 g of silica gel in n-hexane/benzene solvent mixture as elution solvent to obtain the final product as white solid (m.p. 34.0°–35.0° C.). Yield: 8.8 g.

Elementary analysis as C₅₀H₈₂O₂:

| | C | H |
|---|---|---|
| Theoretical (%): | 83.97 | 11.56 |
| Found (%): | 83.95 | 11.57 |

MAS Spectrum: M+ 752

IR Spectrum: (cm⁻¹) 2945, 1735, 1670, 1450, 1385, 1175

NMR Spectrum: (CDCl₃, ppm)

| | | | |
|---|---|---|---|
| 0.88 | t | 3H | —CH₃ |
| 1.24–1.50 | m | 4H | —CH₂— |
| 1.58, 1.68 | s | 30H | $\overset{\mid}{-C}=\overset{\mid}{C}-CH_3$ |
| 1.98–2.04 | m | 32H | $\overset{\mid}{-C}=\overset{\mid}{C}-CH_2-$ |
| 2.27 | t | 2H | $-\overset{\overset{\displaystyle \parallel}{O}}{C}-CH_2-$ |
| 4.52 | d | 2H | $\overset{\mid}{-C}=\overset{\mid}{C}-CH_2-O-$ |
| 5.05–5.28 | m | 9H | $\overset{\mid}{-C}=CH$ |

SYNTHESIS EXAMPLE 8

3,7,11,15,19,23,27,31,35,39-Decamethyl-2,6,10,14,18,22,26,30,34,38-tetracontaenyl acrylate 8.0 Grams of decaprenol were dissolved in 50 ml of pyridine. The solution was added with 15% solution of 2.1 g of acrylic acid chloride in pyridine at room temperature over 30 minutes. After completion of the addition, the mixture was stirred at room temperature for two hours to complete the reaction. The reaction product was diluted with n-hexane, washed with water and concentrated. The concentrate was purified by chromatography with 80 g of silica gel in n-hexane/benzene solvent mixture as elution solvent to obtain white solid (m.p. 32.0°–32.8° C.). Yield 5.8 g.

Elementary analysis as C₅₃H₈₄O₂:

| | C | H |
|---|---|---|
| Theoretical (%): | 84.51 | 11.24 |
| Found (%): | 84.49 | 11.25 |

MAS Spectrum: M+ 752

IR Spectrum: (cm⁻¹) 2940, 1730, 1670, 1450, 1410, 1390, 1190, 810

NMR Spectrum: (CDCl₃, ppm)

| | | | |
|---|---|---|---|
| 1.60, 1.68, 1.72 | s | 30H | $\overset{\mid}{-C}=\overset{\mid}{C}-CH_3$ |
| 2.02 | m | 36H | $\overset{\mid}{-C}=\overset{\mid}{C}-CH_2-$ |
| 4.65 | d | 2H | $\overset{\mid}{-C}=\overset{\mid}{C}-CH_2-O-$ |
| 5.08–5.32 | m | 10H | $\overset{\mid}{-C}=CH$ |
| 5.68–6.44 | m | 3H | $-\overset{\mid}{CH}=CH_2$ |

SYNTHESIS EXAMPLE 9

3,7,11,15,19,23,27,31,35-Nonamethyl-2,6,10,14,18,22,26,30,34-hexacontanonaenyl-p-chlorobenzoate 8.0 Grams of solanesol were dissolved in 30 ml of pyridine. The solution was added with 15% solution of 4.5 g of p-chlorobenzoyl chloride in pyridine dropwise at room temperature over 30 minutes. After completion of the addition, the mixture was stirred at room temperature for two hours to complete the reaction. The reaction product was diluted with n-hexane, washed with water and concentrated. The concentrate was purified by chromatography with 80 g of silica gel in n-hexane/benzene solvent mixture as elution solvent to obtain the final product as white solid (m.p. 30.5°–31.5° C.). Yield: 6.0 g.

Elementary analysis as C₅₂H₇₇ClO₂:

| | C | H | Cl |
|---|---|---|---|
| Theoretical (%): | 81.15 | 10.09 | 4.61 |
| Found (%): | 81.13 | 10.10 | 4.59 |

MAS Spectrum: M+ 768, 770

IR Spectrum: (cm⁻¹) 2930, 1725, 1670, 1600, 1495, 1450, 1385, 1275, 1095, 850, 760

NMR Spectrum: (CDCl₃, ppm)

| | | | |
|---|---|---|---|
| 1.56, 1.65, 1.74 | s | 30H | $\overset{\mid}{-C}=\overset{\mid}{C}-CH_3$ |
| 1.98–2.07 | m | 32H | $\overset{\mid}{-C}=\overset{\mid}{C}-CH_2-$ |
| 4.76 | d | 2H | $\overset{\mid}{-C}=\overset{\mid}{C}-CH_2-O-$ |
| 5.05–5.39 | m | 9H | $\overset{\mid}{-C}=CH$ |
| 7.31–7.89 | m | 4H | 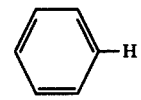 |

SYNTHESIS EXAMPLE 10

3,7,11,15,19,23,27,31,35,39,43-Undecamethyl-2,6,10,14,18,22,26,30,34,38,42-tetratetracontaundecaenyl acetate 3.5 Grams of undecaprenol were dissolved in 15 ml of acetic acid anhydride and the solution was added with 2.0 g of anhydrous sodium acetate at room temperature. The mixture was stirred at 100° C. for one hour to complete the reaction. Upon cooling, the reaction product was poured in water to hydrolyze excessive acetic acid anhydride. After extraction with n-hexane, the extract was washed with water and concentrated. The concentrate was purified by chromatography with 50 g of silica gel in n-hexane/benzene solvent mixture as elution solvent to obtain the final product as white solid (m.p. 36.0°–37.0° C.). Yield 3.5 g.

| Elementary analysis as $C_{57}H_{92}O_2$: | | |
|---|---|---|
| | C | H |
| Theoretical (%): | 84.59 | 11.46 |
| Found (%): | 84.61 | 11.46 |

MAS Spectrum: M+ 808
IR Spectrum: (cm$^{-1}$) 2940, 1745, 1670, 1450, 1390, 1370, 1235, 1030
NMR Spectrum: (CDCl$_3$, ppm)

| 1.58, 1.68 | s | 36H | $-\overset{\mid}{C}=\overset{\mid}{C}-CH_3$ |
|---|---|---|---|
| 2.00 | m | 40H | $-\overset{\mid}{C}=\overset{\mid}{C}-CH_2-$ |
| 2.02 | s | 3H | $-\overset{O}{\overset{\parallel}{C}}-CH_3$ |
| 4.53 | d | 2H | $-\overset{\mid}{C}=\overset{\mid}{C}-CH_2-O-$ |
| 5.08–5.30 | m | 11M | $-\overset{\mid}{C}=CH-$ |

SYNTHESIS EXAMPLE 11

3,7,11,15,19,23,27,31,35,39,43-Undecamethyl-2,6,10,14,18,22,26,30,34,38,42-tetratetracontaundecaenyl benzoate 3.5 Grams of undecaprenol were dissolved in 30 ml of pyridine and the solution was added with a solution of 1.3 g of benzoyl chloride in pyridine dropwise over 30 minutes. After completion of the addition, the mixture was stirred at room temperature for one hour to complete the reaction. The reaction product was diluted with n-hexane, washed with water and concentrated. The concentrate was purified by chromatography with 50 g of silica gel in n-hexane/benzene solvent mixture as elution solvent to obtain white waxy final product. Yield: 3.6 g.

| Elementary analysis as $C_{62}H_{94}O_2$: | | |
|---|---|---|
| | C | H |
| Theoretical (%): | 85.45 | 10.87 |
| Found (%): | 85.43 | 10.86 |

MAS Spectrum: M+ 870
IR Spectrum: (cm$^{-1}$) 2940, 1800, 1725, 1670, 1605, 1455, 1385, 1275, 1105, 710
NMR Spectrum: (CDCl$_3$, ppm):

| 1.56, 1.64, 1.73 | s | 36H | $-\overset{\mid}{C}=\overset{\mid}{C}-CH_3$ |
|---|---|---|---|
| 1.96–2.06 | m | 40H | $-\overset{\mid}{C}=\overset{\mid}{C}-CH_2-$ |
| 4.76 | d | 2H | $-\overset{\mid}{C}=\overset{\mid}{C}-CH_2-O-$ |
| 5.04–5.20 | m | 11H | $-\overset{\mid}{C}=CH$ |
| 7.40–7.96 | m | 2H | 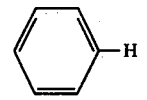 |

SYNTHESIS EXAMPLE 12

3,7,11,15,19,23,27,31,35-Nonamethyl-2,6,10,14,18,22,26,30,34-hexatriacontanonaenyl nicotinate 10 Grams of solanesol were dissolved in 50 ml of pyridine and the solution was added with a solution of 4.5 g. of nicotinic acid chloride in pyridine dropwise over 30 minutes. After completion of the addition, the mixture was stirred at room temperature for two hours to complete the reaction. The reaction product was diluted with-hexane, washed with water and concentrated. The concentrate was purified by chromatography with 80 g. of silica gel in n-hexane/ether solvent mixture as elution solvent to obtain white yellow waxy final product. Yield 6.5 g.

| Elementary analysis as $C_{51}H_{77}NO_2$: | | | |
|---|---|---|---|
| | C | H | N |
| Theoretical (%): | 83.21 | 10.54 | 1.90 |
| Found (%): | 83.18 | 10.55 | 1.92 |

MAS Spectrum: M+ 735
IR Spectrum: (cm$^{-1}$) 2930, 1740, 1595, 1450, 1385
NMR Spectrum: (CDCl$_3$, ppm)

| 1.57, 1.68 | s | 30H | $-\overset{\mid}{C}=\overset{\mid}{C}-CH_3$ |
|---|---|---|---|
| 1.99–2.04 | m | 32H | $-\overset{\mid}{C}=\overset{\mid}{C}-CH_2-$ |
| 4.73 | d | 2H | $-\overset{\mid}{C}=\overset{\mid}{C}-CH_2-O-$ |
| 5.05–5.25 | m | 9H | $-\overset{\mid}{C}=CH$ |
| 7.5–9.5 | m | 4H | pyridyl |

SYNTHESIS EXAMPLE 13

3,7,11,15,19,23,27,31,35-Nonamethyl-2,6,10,14,18,22,26,30,34-hexatriacontanonaenyl propionate 6.3 Grams of solanesol and 1.6 g. of propionic acid anhydride were dissolved in pyridine and the solution was stirred at 80° C. for 5 hours. After completion of the reaction, the reaction product was poured in water to hydrolyze excessive propionic acid anhydride. After extraction with n-hexane, the extract was washed with water and n-hexane layer was subjected to distillation under reduced pressure. The residual oily substance was purified by column chromatography with 50 g. of silica gel to obtain the final product as white solid (m.p. 33°-35° C.). Yield 6.5 g. (93.4%).

| Elementary analysis as $C_{48}H_{78}O_2$: | | |
|---|---|---|
| | C | H |
| Theoretical (%): | 83.96 | 11.37 |
| Found (%): | 83.91 | 11.40 |

MAS Spectrum: M+ 686
IR Spectrum: (cm$^{-1}$) 2945, 1735, 1670, 1450, 1385, 1175
NMR Spectrum: (CDCl$_3$, ppm)

| 1.10 | t | 3H | —CH$_3$ |
|---|---|---|---|
| 1.58, 1.68 | s | 30H | $-\overset{\mid}{C}=\overset{\mid}{C}-CH_3$ |
| 1.98-2.04 | m | 32H | $-\overset{\mid}{C}=\overset{\mid}{C}-CH_2-$ |
| 2.30 | q | 2H | $-\underset{O}{\overset{\parallel}{C}}-CH_2-$ |
| 4.52 | d | 2H | $-\overset{\mid}{C}=\overset{\mid}{C}-CH_2-O-$ |
| 5.0-5.08 | m | 9H | $-\overset{\mid}{C}=CH$ |

SYNTHESIS EXAMPLE 14

3,7,11,15,19,23,27,31,35-Nonamethyl-2,6,10,14,18,22,26,30,34-hexatriacontanonaenyl stearate 16 Grams of solanesol, 7.5 g. of stearic acid and 10 g. of polyphosphoric acid ethyl ester were dissolved in 40 ml of chloroform and the solution was refluxed under stirring for 4 hours. After completion of the reaction, the reaction product was poured in water and added with about 10 g. of sodium hydrogencarbonate to decompose the polyphosphoric acid ester. After extraction with ether, the ether layer was washed with water and subjected to distillation under reduced pressure. The residual oily substance was purified by column chromatography with 100 g. of silica gel to obtain 12.5 g. (54.8%) of white solid (m.p. 36°-37° C.).

| Elementary analysis as $C_{63}H_{108}O_2$: | | |
|---|---|---|
| | C | H |
| Theoretical (%): | 84.31 | 12.13 |
| Found (%): | 84.27 | 12.11 |

MAS Spectrum: M+ 896
IR Spectrum: (cm$^{-1}$) 2945, 1735, 1670, 1450, 1385, 1175
NMR Spectrum: (CDCl$_3$, ppm)

| 0.88 | t | 3H | —CH$_3$ |
|---|---|---|---|
| 1.25 | m | 32H | —CH$_2$— |
| 1.58, 1.68 | s | 30H | $-\overset{\mid}{C}=\overset{\mid}{C}-CH_3$ |
| 1.98-2.04 | m | 32H | $-\overset{\mid}{C}=\overset{\mid}{C}-CH_2-$ |
| 2.20 | m | 2H | $-\underset{O}{\overset{\parallel}{C}}-CH_2-$ |
| 4.52 | d | 2H | $-\overset{\mid}{C}=\overset{\mid}{C}-CH_2-O-$ |
| 5.0-5.08 | m | 9H | $-\overset{\mid}{C}=CH$ |

SYNTHESIS EXAMPLE 15

3,7,11,15,19,23,27,31,35-Nonamethyl-2,6,10,14,18,22,26,30,34-hexatriacontanonaenyl linolate 16 Grams of solanesol, 7.5 g. of linoleic acid and 10 g. of polyphosphoric acid ethyl ester were dissolved in 40 ml of chloroform and the solution was refluxed under stirring for four hours. After completion of the reaction, the reaction product was poured in water and added with 10 g. of sodium hydrogencarbonate to decompose the polyphosphoric acid ethyl ester. After extraction with ether, the ether layer was washed with water and subjected to distillation under reduced pressure. The residual oily substance was purified by column chromatography with 100 g. of silica gel to obtain 19 g. (80.6%) of colorless oily product.

| Elementary analysis as $C_{63}H_{104}O_2$: | | |
|---|---|---|
| | C | H |
| Theoretical (%): | 84.69 | 11.73 |
| Found (%): | 84.59 | 11.72 |

MAS Spectrum: M+ 892
IR Spectrum: (cm$^{-1}$) 2945, 1735, 1670, 1450, 1385
NMR Spectrum: (CDCl$_3$, ppm)

| 0.88 | t | 3H | —CH$_3$ |
|---|---|---|---|
| 1.30 | m | 16H | —CH$_2$— |
| 1.58, 1.68 | s | 30H | $-\overset{\mid}{C}=\overset{\mid}{C}-CH_3$ |
| 1.98-2.04 | m | 36H | $-\overset{\mid}{C}=\overset{\mid}{C}-CH_2-$ |
| 2.23 | m | 2H | $-\underset{O}{\overset{\parallel}{C}}-CH_2-$ |
| 2.75 | m | 2H | $-\overset{\mid}{C}-CH_2-\overset{\mid}{C}=$ |
| 4.52 | d | 2H | $-\overset{\mid}{C}=\overset{\mid}{C}-CH_2-O-$ |
| 5.0-5.08 | m | 9H | $-\overset{\mid}{C}=CH$ |
| 5.28 | m | 4H | $-\overset{\overset{H}{\mid}}{C}=\overset{\overset{H}{\mid}}{C}-$ |

In the following examples, recipes wherein 3,7,11,15,19,23,27,31,35-nonamethyl-2,6,10,14,18,22,26,30,34-hexatriacontane-1-ol (hereinafter referred to as the basis) which is one of the compounds according to the present invention is used are given.

EXAMPLE 1 (Capsules)

| | |
|---|---|
| Basis | 5 g |
| Microcrystalline cellulose | 80 g |
| Corn starch | 20 g |
| Lactose | 22 g |

| | |
|---|---|
| -continued | |
| Polyvinylpyrrolidone | 3 g |
| Total | 130 g |

The above components were granulated according to a conventional method and the resulting granules were filled in 1,000 gelatin hard capsules. Each capsule contained 5 mg of the basis.

EXAMPLE 2 (POWDERS)

| | |
|---|---|
| Basis | 50 g |
| Microcrystalline cellulose | 400 g |
| Corn starch | 550 g |
| Total | 1000 g |

The basis was dissolved in acetone and the solution was adsorbed on microcrystalline cellulose. The cellulose was then dried and mixed with corn starch. The mixture was formed into powders according to a conventional method to obtain powders of 1/20 concentration.

EXAMPLE 3 (TABLETS)

| | |
|---|---|
| Basis | 5 g |
| Corn starch | 10 g |
| Lactose | 20 g |
| Calcium carboxymethylcellulose | 10 g |
| Microcrystalline cellulose | 40 g |
| Polyvinylpyrrolidone | 5 g |
| Talc | 10 g |
| Total | 100 g |

The basis was dissolved in acetone and the solution was adsorbed on microcrystalline cellulose. The cellulose was dryed and mixed with corn starch, lactose and calcium carboxymethylcellulose. The mixture was added with an aqueous polyvinylpyrrolidone solution as binder and granulated according to a conventional method. The resulting granules were mixed with talc as a lubricant and formed into tablets, each having a weight of 100 mg and containing 5 mg of the basis.

EXAMPLE 4 (INJECTIONS)

| | |
|---|---|
| Basis | 10 g |
| Nikkol HCO-60 (a product of Nikko Chemical Co.) | 37 g |
| Sesame oil | 2 g |
| Sodium chloride | 9 g |
| Propylene glycol | 40 g |
| Phosphate buffer (0.1 M, pH 6.0) | 100 ml |
| Distilled water | balance |
| Total | 1000 ml |

A mixture of the basis, Nikkol HCO-60, Sesame oil and a half amount of propylene glycol was heated at about 80° C. to obtain the solution. The solution was mixed with the phosphate buffer and distilled water in which sodium chloride and propylene glycol had been dissolved and which had been pre-heated to about 80° C. to form 1000 ml of an aqueous solution. The aqueous solution was charged in 2 ml ampoules. The ampoules were melt-sealed and sterilized under heating.
Each ampoule contained 20 mg of the basis.

The embodiments of the invention in which an exclusive property or privilege is claimed are defined as follows:

1. A method of treating hypertension which comprises orally or parenterally administering to a hypertensive subject requiring such treatment, a therapeutically effective amount of a hypertension treating composition comprising a pharmaceutical carrier and an effective anti-hypertensive amount of polyprenyl alcohol compound having the formula:

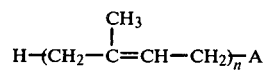

wherein n is an integer of 7–10, and A is a group of the formula:

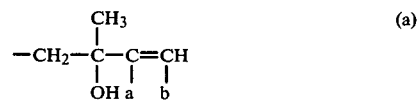

in which a and b each is hydrogen or a and b together form a valence bond between the carbon atoms to which they are attached, or

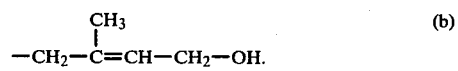

2. A method according to claim 1 wherein said polyprenyl alcohol compound is 3,7,11,15,19,23,27,31,35-nonamethyl-1,6,10,14,18,22,26,30,34-hexatriacontanonaene-3-ol.

3. A method according to claim 1 wherein said polyprenyl alcohol compound is 3,7,11,15,19,23,27,31,35,39-decamethyl-1,6,10,14,18,22,26,30,34,38-tetracontadecaene-3-ol.

4. A method according to claim 1 wherein said polyprenyl alcohol compound is 3,7,11,15,19,23,27,31,35,39,43-Undecamethyl-1,6,10,14,18,22,26,30,34,38,42-tetratetracontaundecaene-3-ol.

5. A method according to claim 1 wherein said polyprenyl alcohol compound is 3,7,11,15,19,23,27,31,35-Nonamethyl-6,10,14,18,22,26,30,34-hexatriacontaoctaene-1-yn-3-ol.

6. A method according to claim 1 wherein said polyprenyl alcohol compound is 3,7,11,15,19,23,27,31,35,39-decamethyl-6,10,14,18,22,26,30,34,38-tetracontanonaene-1-yn-3-ol.

7. A method according to claim 1 wherein said polyprenyl alcohol compound is 3,7,11,15,19,23,27,31,35,39,43-undecamethyl-6,10,14,18,22,26,30,34,38,42-tetratetracontadecaene-1-yn-3-ol.

8. A method according to claim 1 wherein said polyprenyl alcohol compound is 3,7,11,15,19,23,27,31-octamethyl-2,6,10,14,18,22,26,30-dotriacontaoctaene-1-ol.

9. A method according to claim 1 wherein said polyprenyl alcohol compound is 3,7,11,15,19,23,27,31,35-nonamethyl-2,6,10,14,18,22,26,30,34-hexatriacontanonaene-1-ol.

10. A method according to claim 1 wherein said polyprenyl alcohol compound is 3,7,11,15,19,23,27,31,35,39-decamethyl-2,6,10,14,18,22,26,30,34,38-tetracontadecaene-1-ol.

11. A method according to claim 1 wherein said polyprenyl alcohol compound is 3,7,11,15,19,23,27,31,35,39,43-undecamethyl-2,6,10,14,18,22,26,30,34,38,42-undecaene-1-ol.

12. A method according to claim 1 in which A is

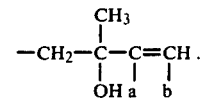

13. A method according to claim 1 in which A is

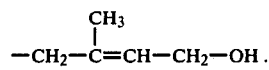

14. A method according to claim 1 in which the amount of said polyprenyl alcohol compound administered is from 10 to 200 mg/day.

15. A method according to claim 14 in which said hypertension treating composition is orally administered.

* * * * *